United States Patent [19]

Ikeura

[11] 4,172,247
[45] Oct. 23, 1979

[54] GAS CONCENTRATION SENSING DEVICE

[75] Inventor: Kenji Ikeura, Yokosuka, Japan

[73] Assignee: Nissan Motor Company, Limited, Yokohoma, Japan

[21] Appl. No.: 842,874

[22] Filed: Oct. 17, 1977

[30] Foreign Application Priority Data

Oct. 18, 1976 [JP] Japan ................. 51-123855

[51] Int. Cl.² .......................................... G01N 27/28
[52] U.S. Cl. ........................................ 338/34; 73/23;
73/27 R; 204/195 S; 422/98
[58] Field of Search ............. 338/34; 23/254 E; 73/23, 27 R; 204/195 S

[56] References Cited

U.S. PATENT DOCUMENTS

| | | | |
|---|---|---|---|
| 2,787,903 | 4/1957 | Beard | 73/23 |
| 2,811,037 | 10/1957 | Beard | 73/23 |
| 3,738,341 | 6/1973 | Loos | 123/119 E |
| 3,768,259 | 10/1973 | Carnahan | 204/195 S X |
| 3,819,500 | 6/1974 | Esdonk | 204/195 S |
| 3,844,920 | 10/1974 | Burgett | 204/195 S |
| 3,864,628 | 2/1975 | Klass | 73/23 X |
| 3,869,370 | 3/1975 | Sayles | 73/23 X |
| 3,935,089 | 1/1976 | Togawa | 204/195 S |
| 4,033,170 | 7/1977 | Kawamura | 73/23 |

Primary Examiner—Richard R. Kucia
Attorney, Agent, or Firm—Schwartz, Jeffery, Schwaab, Mack, Blumenthal & Koch

[57] ABSTRACT

A gas concentration sensing device has a plate type sensing element which is equipped with first and second electrodes which are exposed to first and second gases, respectively. A chamber is formed adjacent to the sensing element so that the leaked first gas is introduced into the chamber so as to prevent the leaked first gas from contacting the second electrode.

20 Claims, 4 Drawing Figures

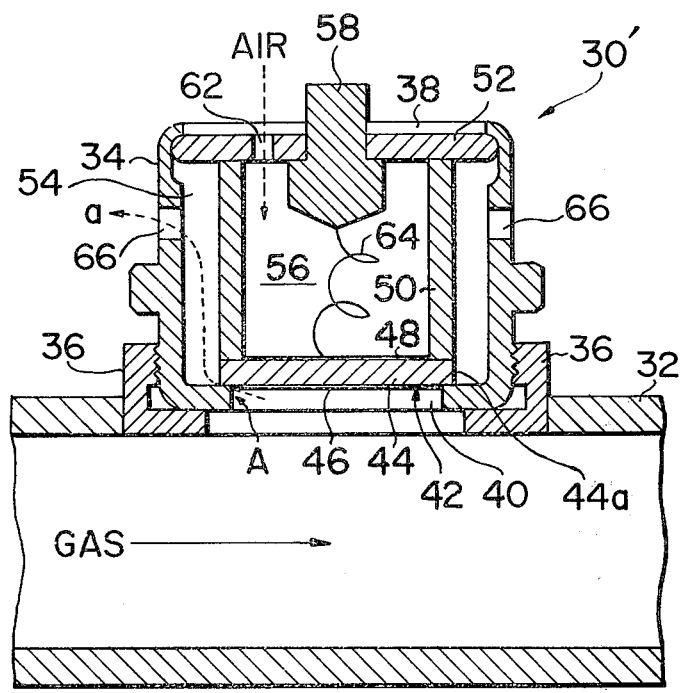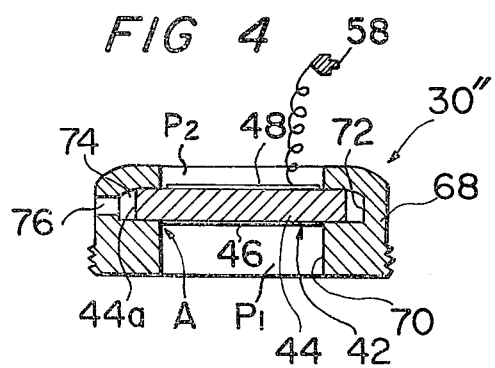

GAS CONCENTRATION SENSING DEVICE

BACKGROUND OF THE INVENTION

This invention relates to a gas concentration sensing device for generating an electric signal representing the concentration of a gaseous component in a mixed gas, and more particularly to an oxygen concentration sensor for detecting the oxygen concentration in the exhaust gas of an internal combustion engine.

SUMMARY OF THE INVENTION

It is the principal object of the present invention to provide an improved gas concentration sensing device of the type wherein a plate type sensing element is employed, by which problems encountered in the prior art are solved.

Another object of the present invention is to provide an improved gas concentration sensing device of the type wherein a plate type sensing element is employed, in which the problems due to gas leakage are solved although a strict gastight seal is not provided between the sensing element and holding means for securely holding the sensing element.

A further object of the present invention is to provide an improved gas sensing device of the type wherein a plate type sensing element is provided with two electrodes at the two flat surfaces thereof, in which a chamber is formed between the two electrodes to prevent gas exposed to one electrode from contacting with the other electrode.

A still further object of the present invention is to provide an improved oxygen concentration sensing device for sensing the oxygen concentration in the exhaust gas of the type wherein a plate type sensing element is used, which demonstrates high performance and durability and is easy and inexpensive to produce.

Other objects, features, and advantages of the gas concentration sensing device according to the present invention will become more apparent from the following description taken in conjunction with the attached drawings.

BRIEF DESCRIPTION OF THE DRAWINGS

In the Drawings:

FIG. 3 is a schematic section view of another preferred embodiment of a gas concentration sensing device according to the present invention; and FIG. 4 is a schematic section view of a further preferred embodiment of a gas concentration sensing device in accordance with the present invention.

DETAILED DESCRIPTION OF PREFERRED EMBODIMENTS

Figure 1:
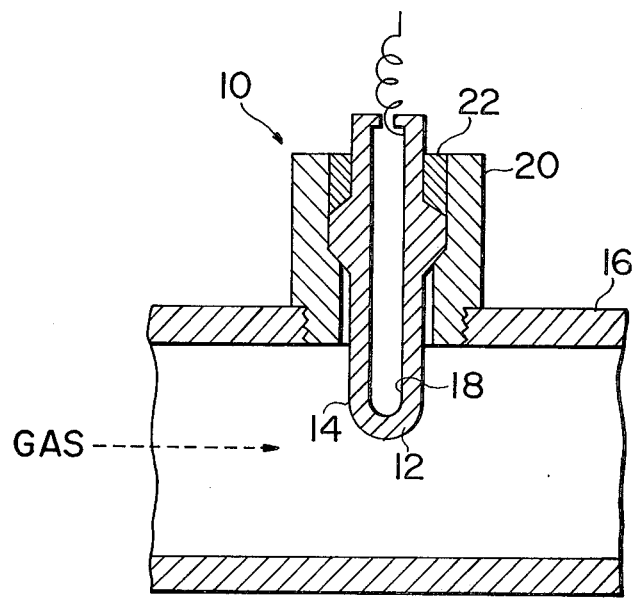
FIG. 1 is a schematic section view of an example of a prior art gas concentration sensing device.

Referring to FIG. 1 of the drawings, an oxygen concentration sensor 10 is shown as an example of a prior art gas concentration sensor for generating an electric signal representing the difference in the concentrations of a gaseous component contained in two separate gases. The oxygen concentration sensor 10 is composed of a sensing element 12 which is in the shape of a tube having one end closed. As shown, the other end of the tube is also partially closed, maintaining an opening for communicating the interior of the tube with the atmospheric air. The sensing element 12 is made of a solid electrolyte of stabilized zirconia ($ZrO_2$) ceramic through which oxygen ions pass. The outer surface of the sensing element 12 is coated with a porous platinum electrode layer 14 which is exposed to the stream of a gas flowing through a pipe 16. The inner surface of the sensing element 12 is also coated with a porous platinum electrode layer 18 which is exposed to the atmospheric or ambient air.

The sensing element 12 is secured in a holder 20 which is, in turn, securely screwed into the wall of the pipe 16. Disposed between the sensing element 12 and the holder 20 is a sealing member 22 for preventing the gas flowing in the pipe 16 from leaking into the atmospheric air.

With this arrangement, if there are different partial pressures of oxygen on both sides of the tube of the sensing element 12, an electrical potential builds up across the platinum electrodes and accordingly produces an electrical signal representing the difference of oxygen gas concentration between the atmosphere and the gas flowing through the pipe 16.

However, this type of the gas concentration sensor has encountered the following problem: it is rather difficult to produce the sensing element 12 in the shape of the tube having one closed end and therefore the sensing element inevitably becomes expensive. Furthermore, although only the tip portion of the sensing element 12 functions to sense the gas concentration, it is required to use very expensive platinum electrode and solid electrolyte material on surfaces which do not function to sense the gas concentration. This is very wasteful from the point of view of conservation of natural resources.

In order to solve the above-mentioned problems, it has been proposed to use a solid electrolyte sensing element which is formed in the shape of a plate. However, achieving a gastight seal with such a shaped sensing element in a holder is very difficult. Therefore a sensor including a sensing element in a plate shape has until now exhibited poor operational characteristics. To improve the gastight seal, the construction of the sensor inevitably becomes very complex and therefore high precision production is required.

The present invention solves the above-mentioned problems encountered in the prior art gas concentration sensor and to provide an improved gas concentration sensor of the type wherein a sensing element formed in a plate type is used.

Figure 2:
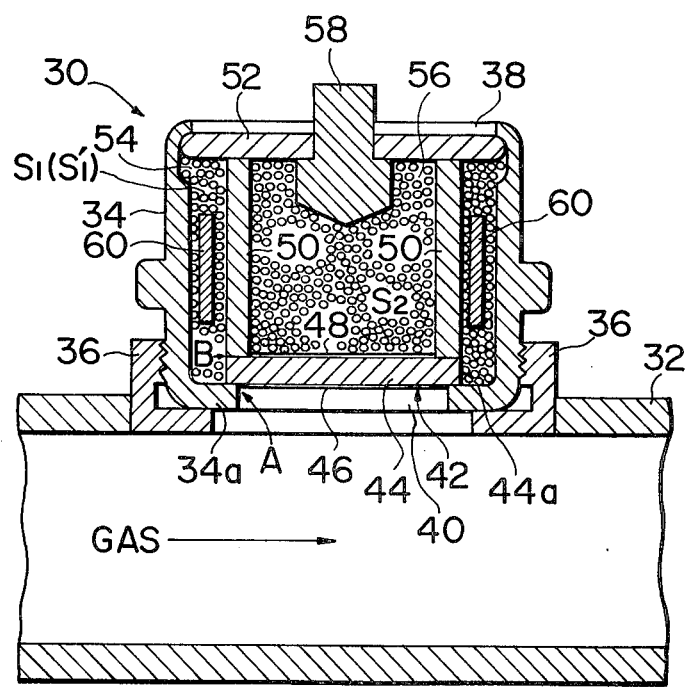
FIG. 2 is a schematic section view of a preferred embodiment of a gas concentration sensing device in accordance with the present invention.

Referring now to FIG. 2 of the drawings, there is shown a preferred embodiment of a gas concentration sensing device 30 or a gas concentration sensor. In this instance, the gas concentration sensor 30 is an oxygen gas concentration sensor which generates an electrical signal in accordance with the concentration of oxygen gas present in a gas flowing through a pipe 32 such as an exhaust pipe of an internal combustion engine.

The gas concentration sensor 30 is composed of a cylindrical metallic casing 34 which is screwed into an annular securing member 36 which is, in turn, fixed to the wall of the pipe 32. The cylindrical casing 34 is formed with an opening 38 at its one end or upper end. An radial annular flange portion 34a is provided at the other end of the casing 34 to define an opening 40 by its inner peripheral edge. As shown, the opening 40 communicates with the interior of the pipe 32 through an opening (no numeral) defined by the annular securing member 36.

A sensing element 42 is disposed within the casing and on the inner surface of the flange portion 34a of the casing 34 so as to close the opening 40. The sensing element 42 consists of a flat circular plate 44 of a solid electrolyte through which oxygen ions pass. The solid electrolyte is, for example, of stabilized zirconia ($ZrO_2$). As seen, the flat plate 44 contacts at its bottom flat surface with the inner surface of the casing flange portion 34a to define a contact surface A. The bottom flat surface of the flat plate 44 is coated with a thin layer of a porous platinum electrode 46 to form a first electrode so that the first electrode 46 contacts the gas flowing in the pipe 32 through the opening 40 defined by the annular securing member 36. Furthermore, the top flat surface of the flat plate 44 is also coated with a thin layer of a porous platinum electrode 48 to form a second electrode, except for its portion which contacts a ceramic sleeve member 50 to define a contact surface B. The sleeve member 50 is interposed between the flat plate 44 of the sensing element 42 and a lid member 52 or a pad closing the opening formed at the upper end of the casing 34. The sleeve member 50 is located spaced apart from the inner surface of the casing 34 and divides the inside of the casing into an outer chamber 54 and an inner chamber 56. With this connection, the sensing element 42 is located so that the end surface 44a of the flat plate is opposite to and spaced apart from the inner surface of the cylindrical wall of the casing 34 to define a lower portion of the outer chamber 54.

Packed in the outer chamber 54 is a substance $S_1$ for absorbing the gas from the pipe 36 which leaks in via the contact surface A which substance is, for example, activated carbon particles. The outer chamber 54 may alternatively be packed with a kind of catalyst $S_1'$ for catalytically converting the gas flowing in the pipe 32 into a gas or a substance which does not affect the second electrode 48.

Packed in the inner chamber 56 is a substance $S_2$ for providing a partial pressure of oxygen gas on the second electrode 48 and which substance is, for example, a mixture of powdered Nickel (Ni) and Nickel oxide ($NiO_2$), or sintered metal made of a mixture of Ni and $NiO_2$.

The reference numeral 58 represents a terminal which is electrically connected through the substance $S_2$ to the second electrode 48 in order to pick up the electrical potential built up at the electrodes 46 and 48. In this instance, the first electrode 46 is grounded through the casing 34. The terminal 58 may be electrically connected to a control circuit (not shown) for controlling the operations of various devices in accordance with the electrical potential picked up by the terminal 58.

It will be understood from the foregoing, that when there are different partial pressures of oxygen on both sides of the sensing element 42, an electrical potential builts up in the sensing element 42 to generate an electrical signal representing or corresponding to the difference in oxygen gas concentration between the gas present in the inner chamber 56 and the gas flowing in the pipe 32.

With the gas concentration sensing device shown in FIG. 2, since the contact surfaces A and B communicate with each other through the outer chamber 54, the gas flowing in the pipe 32 does not reach, maintaining its high concentration condition, to the second electrode 48 if the gas flowing in the pipe 32 leaks into the outer chamber 54 through the contact surface A in which a small clearance or opening is formed. Consequently, a completely gastight seal is not necessary at the contact surface A. In this connection, it is difficult to provide a strict gastight seal to the contact surface A, because the contact surface A is generally formed by contact of a metal and a porous ceramic material, and because the contact surface A is subject to a high temperature at which use of sealants for sealing the contact surface A is impossible.

In order to further improve the effect for preventing the gas flowing in the pipe 32 from leaking into contact with the second electrode 48, the contact surface B is preferably sealed with a sealant of a vitreous material or of a ceramic cement. Furthermore, it is preferable for improving the above-mentioned effect to use heating means 60 for heating the substance $S_1$ or $S_1'$ packed in the outer chamber 54 so as to increase the absorbing ability or converting ability with respect to the gas which leaks into the outer chamber 54.

FIG. 3 shows another preferred embodiment of the gas concentration sensor 30' according to the present invention, which is essentially similar to the embodiment of FIG. 2 and, as such, like reference numerals are assigned to corresponding parts.

In this embodiment, the inner chamber 56 does not contain any substance and is vacant. However, the inner chamber 56 communicates with the atmosphere through an opening 62 formed through the lid member 52. Additionally, the terminal 58 is connected directly or through a conductor 64 to the second electrode 48. Therefore, as before this gas concentration sensor is arranged to generate an electrical signal representing the difference in oxygen gas concentration between the atmosphere and the gas flowing in the pipe 32.

Moreover, the outer chamber 54 also does not contain any substance and is vacant. The cylindrical wall of the casing 34 is provided with openings 66 through which the outer chamber 54 communicates with the atmosphere. With the thus arranged device, when the gases leaks from the inside of the pipe 32 through the contact surface A into the outer chamber 54, the gas is allowed to escape through the opening 66 into the atmosphere. Therefore the gas leaked from the pipe 32 does not affect the second electrode 48.

While the sensing element 42 has been shown and described as located outside of the level of the wall of the pipe 32 in the embodiments shown in FIGS. 2 and 3, it will be appreciated that sensing element 42 may be readily located inside of the level of the wall of the pipe 32 by modifying the shapes of the casing 34 and the securing member 36. Although the casing 34 and sensing element 42 are shown and described to be formed in a cylindrical shape and a disc shape, respectively, in the embodiments in FIGS. 2 and 3, it will be appreciated that they may be formed into other shapes in consideration of various circumstances.

FIG. 4 shows a further preferred embodiment of the gas concentration sensor 30" which is composed of a cylindrical metallic holder 68 for holding the sensing element 42 which is similar to that of FIGS. 2 and 3. The cylindrical holder 68 is formed with a cylindrical bore 70 or an opening. Formed along the inner peripheral surface of the cylindrical bore 70 is an annular groove 72 which is merged into the cylindrical bore 70.

The peripheral portion of the flat circular plate 44 of sensing element 42 is securely disposed in the annular groove 72 to divide the inside of the cylindrical bore 70 into two portions $P_1$ and $P_2$. It is to be noted that the flat circular plate 44 is located in such a manner that the end surface 44a of the flat circular plate 44 is spaced apart from the surface of the annular groove 72 to form a space 74 or a chamber which communicates with the atmosphere through an opening 76 formed through the wall of the cylindrical holder 68. The holder 68 is secured, via the threaded portion provided thereon, to the wall of the pipe through which a gas such as exhaust gas flows, though not shown. It will be understood that, in the embodiment shown in FIG. 4, the first and second electrodes 46 and 48 are arranged to contact to the gas in the portion $P_1$ and the atmospheric air in the portion $P_2$, respectively, and therefore the sensing element 42 generates an electrical signal representing the difference in oxygen gas concentration between the gas flowing in the pipe 32 and the atmosphere. In this case, the first electrode 46 is electrically connected to the holder 68, while the second electrode 48 is electrically insulated from the holder 68. The second electrode 48 is electrically connected to the terminal 58 through the conductor 64 in order to pick up the electrical potential built up at the electrodes 46 and 48.

With this arrangement, if the gas present in the portion $P_1$ leaks into the space 74 through the contact surface A at which the holder 68 and the plate 44 contact each other, the gas is allowed to escape through the opening 76 into the atmosphere. As a result, the second electrode 48 is not affected by the leaked gas from the portion $P_1$.

What is claimed is:

1. A gas concentration sensing device for generating an electric signal representing the difference in the concentration of a gaseous component contained in separate first and second gases, said gas concentration sensing device comprising:
    a sensing element including a flat plate of a solid electrolyte, a first electrode secured to one flat surface of said flat plate, and a second electrode secured to the other flat surface of said flat plate;
    holding means for holding said sensing element so that the first electrode contacts to the first gas and the second electrode layer contacts to the second gas;
    means for defining a chamber in said holding means, said chamber being located so that the first gas is introduced into said chamber before reaching the second electrode, when the first gas leaks through said holding means; and
    means for lowering the concentration of the first gas introduced into said chamber in order to prevent the first gas introduced into said chamber from reaching the second electrode.

2. A gas concentration sensing device for generating an electric signal representing the difference in the concentration of a gaseous component contained in separate first and second gases, said gas concentration sensing device comprising:
    a casing having first and second openings which are formed opposite to each other, said casing being sealingly secured to a wall inside of which the first gas flows, the first opening directly communicating with an opening formed through the wall;
    a sensing element including a first plate of a ceramic solid electrolyte, a first electrode layer coated on a first flat surface of said flat plate, and a second electrode layer coated on a second flat surface of said flat plate, said sensing element being disposed in said casing to close the first opening of said casing and to allow the first electrode layer to contact to the first gas through the first opening and the opening of the wall;
    a lid member closing the second opening of said casing; and
    a sleeve member having first and second openings formed at its first and second ends, respectively, said sleeve member being interposed between said sensing element and said lid member and spaced apart from the inner surface of said outer casing to divide the inside of said casing into an outer chamber and an inner chamber, the first and second ends of said sleeve member contacting to the second flat surface of the flat plate of said sensing element and an inner surface of said lid member, respectively;
    means for lowering the concentration of the first gas leaked into the outer chamber in order to prevent the first gas leaked into the outer chamber from reaching the second electrode through the inner chamber; and
    a terminal disposed within the inner chamber formed in said casing, said terminal being electrically connected to the second electrode layer coated on the second flat surface of the flat plate of said sensing element.

3. A gas concentration sensing device as claimed in claim 2, in which said casing is formed at its first end with a flange portion which is integral with the wall of said casing, the first opening of said casing being defined by the edge of said flange portion.

4. A gas concentration sensing device as claimed in claim 3, in which said sensing element is so disposed that the first flat surface of the flat plate contact the inner surface of said flange portion, and the side surface of the flat plate is opposite to and spaced apart from the inner surface of said casing to define therebetween a lower portion of the outer chamber within said casing.

5. A gas concentration sensing device as claimed in claim 2, in which said lowering means includes a first substance for absorbing the first gas, said first substance being packed in the outer chamber within said casing to absorb the first gas which leaks into the outer chamber.

6. A gas concentration sensing device as claimed in claim 2, in which said lowering means includes a second substance for catalytically converting the first gas into a gas which does not affect the second electrode layer of said sensing element, said second substance being packed in the outer chamber defined within said casing.

7. A gas concentration sensing device as claimed in claim 5, further comprising a third substance for providing the second gas, packed in the inner chamber within said casing.

8. A gas concentration sensing device as claimed in claim 5, in which said first substance is made of activated carbon.

9. A gas concentration sensing device as claimed in claim 7, in which said third substance is one for providing a partial pressure of oxygen gas on said second electrode layer.

10. A gas concentration sensing device as claimed in claim 9, in which said third substance is a mixture of powdered Ni and $NiO_2$.

11. A gas concentration sensing device as claimed in claim 9, in which said third substance is sintered metal made of a mixture of Ni and $NiO_2$.

12. A gas concentration sensing device as claimed in claim 4, further comprising a heat resistant sealant for sealing a contact surface between the second flat plate of said sensing element and the first end of said sleeve member.

13. A gas concentration sensing means as claimed in claim 12, in which said heat resistant sealant is made of a vitreous material.

14. A gas concentration sensing device as claimed in claim 12, in which said heat resistant sealant is made of a ceramic cement.

15. A gas concentration sensing device as claimed in claim 6, further comprising heating means for heating said second substance.

16. A gas concentration sensing device as claimed in claim 12, in which said lowering means includes an opening formed through the wall of said casing to communicate the outer chamber with the outside of said casing.

17. A gas concentration sensing device as claimed in claim 16, in which said lid member is formed with an opening to communicate the inner chamber with the outside of said casing.

18. A gas concentration sensing device as claimed in claim 16, further comprising an electric conductor connecting said terminal and the second electrode layer of said sensing element.

19. A gas concentration sensing device as claimed in claim 2, in which the wall constitute a part of an exhaust gas pipe of an internal combustion engine, in which the first gas is exhaust gas discharged from the engine.

20. A gas concentration sensing device for generating an electric signal representing the difference in the concentration of a gaseous component contained in separate first and second gases, said gas concentration sensing device comprising:

a holder having an opening therethrough, and a groove formed along the inner peripheral surface of said holder; and a sensing element including a flat plate of a ceramic solid electrolyte, a first electrode layer coated on a first flat surface of said flat plate, and a second electrode layer coated on a second flat surface of said flat plate, said sensing element being securely disposed in the groove of said holder, maintaining a space between the side surface of the flat plate and the inner surface of the groove, said space being in communication with the atmosphere through an opening formed through said holder, the first and second electrode layers contacting the first and second gases, respectively.

* * * * *